United States Patent
Li et al.

(10) Patent No.: US 7,951,580 B2
(45) Date of Patent: May 31, 2011

(54) AUTOMATED, PROGRAMMABLE, HIGH THROUGHPUT, MULTIPLEXED ASSAY SYSTEM FOR CELLULAR AND BIOLOGICAL ASSAYS

(75) Inventors: Guann-Pyng Li, Irvine, CA (US); Mark Bachman, Irvine, CA (US); Nancy Allbritton, Irvine, CA (US); Chris Sims, Irvine, CA (US); Cynthia Jensen-McMullin, Laguna Hills, CA (US)

(73) Assignee: The Regents of the University of California, Oakland, CA (US)

( * ) Notice: Subject to any disclaimer, the term of this patent is extended or adjusted under 35 U.S.C. 154(b) by 385 days.

(21) Appl. No.: 11/112,407

(22) Filed: Apr. 21, 2005

(65) Prior Publication Data
US 2005/0244955 A1 Nov. 3, 2005

Related U.S. Application Data

(60) Provisional application No. 60/564,529, filed on Apr. 21, 2004.

(51) Int. Cl.
*C12Q 1/68* (2006.01)
*C12M 1/00* (2006.01)
*C12M 1/34* (2006.01)
*C12M 3/00* (2006.01)

(52) U.S. Cl. .............. 435/283.1; 435/6; 435/287.2
(58) Field of Classification Search ............ 435/287.2, 435/6, 283.1
See application file for complete search history.

(56) References Cited

U.S. PATENT DOCUMENTS
5,998,129 A 12/1999 Schutze et al.
(Continued)

FOREIGN PATENT DOCUMENTS
WO WO 97/29355 A 8/1997
(Continued)

OTHER PUBLICATIONS

Barron et al., "Laser Printing of Single Cells: Statistical Analysis, Cell Viability, and Stress," Annals of Biomedical Engineering, 33:2, pp. 121-130 (Feb. 2005).

(Continued)

*Primary Examiner* — Walter D Griffin
*Assistant Examiner* — Lydia Edwards
(74) *Attorney, Agent, or Firm* — Orrick, Herrington & Sutcliffe LLP

(57) ABSTRACT

Systems and methods are providing for performing high-throughput, programmable, multiplexed assays of biological, chemical or biochemical systems. Preferably, a micro-pallet includes a small flat surface designed for single adherent cells to plate, a cell plating region designed to protect the cells, and shaping designed to enable or improve flow-through operation. The micro-pallet is preferably patterned in a readily identifiable manner and sized to accommodate a single cell to which it is comparable in size. Each cell thus has its own mobile surface. The cell can be transported from place to place and be directed into a system similar to a flow cytometer. Since, since the surface itself may be tagged (e.g., a bar code), multiple cells of different origin and history may be placed into the same experiment allowing multiplexed experiments to be performed.

23 Claims, 7 Drawing Sheets

U.S. PATENT DOCUMENTS

| | | | |
|---|---|---|---|
| 6,090,919 A | 7/2000 | Cormack et al. | |
| 6,319,668 B1 * | 11/2001 | Nova et al. | 435/6 |
| 6,529,835 B1 * | 3/2003 | Wada et al. | 702/21 |
| 2001/0006815 A1 | 7/2001 | Rabbani et al. | |
| 2003/0059764 A1 * | 3/2003 | Ravkin et al. | 435/4 |
| 2003/0129741 A1 | 7/2003 | Ramstad | |
| 2004/0087052 A1 | 5/2004 | Katakis et al. | |

FOREIGN PATENT DOCUMENTS

| | | |
|---|---|---|
| WO | WO 02/094454 A1 | 11/2002 |
| WO | WO 03/016868 A | 2/2003 |
| WO | WO 03/035824 A | 5/2003 |
| WO | WO 03/039750 A | 5/2003 |
| WO | WO 2004/024328 A | 3/2004 |
| WO | WO 2006041938 A2 | 4/2006 |
| WO | WO 2006060922 A1 | 6/2006 |

OTHER PUBLICATIONS

Langer et al., "Live cell catapulting and recultivation does not change the karyotype of HCT116 tumor cells," Cancer Genetics an Cytogenetics, No. 161 pp. 174-177 (2005).

Stich et al., "Live Cell Catapulting and Recultivation," Pathology Research and Practice, 199:6, pp. 405-409 (Jan. 1, 2003).

Watson, Molecular Biology of the Gene, Third Edition, W.A. Benjamin, Inc., Menlo Park, CA, 1976, p. 62.

Europe, EP 07 79 7210, EP Search Report, Feb. 26, 2009.

Euorpe EP 05 80 2866, EP Search Report Apr. 24, 2009.

Zoeller et al., Strategies for Isolating Somatic Cell Mutants Defective in Liquid Biosynthesis, Methods of Enzymology, vol. 2, pp. 34-51 (1992).

\* cited by examiner

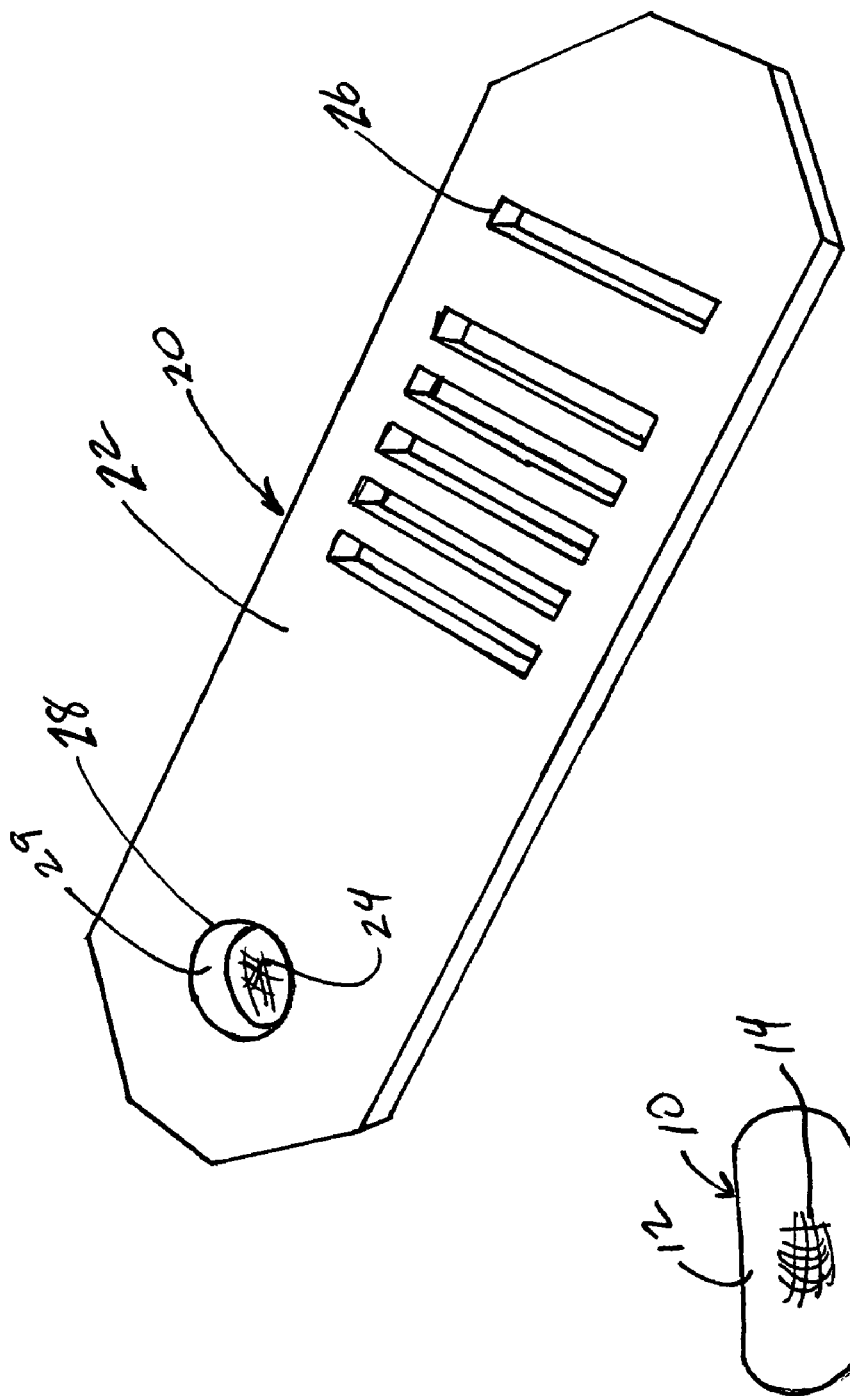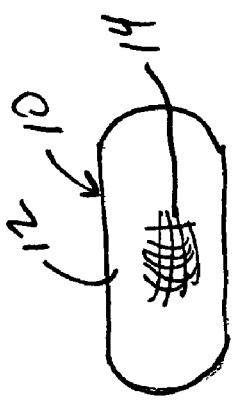

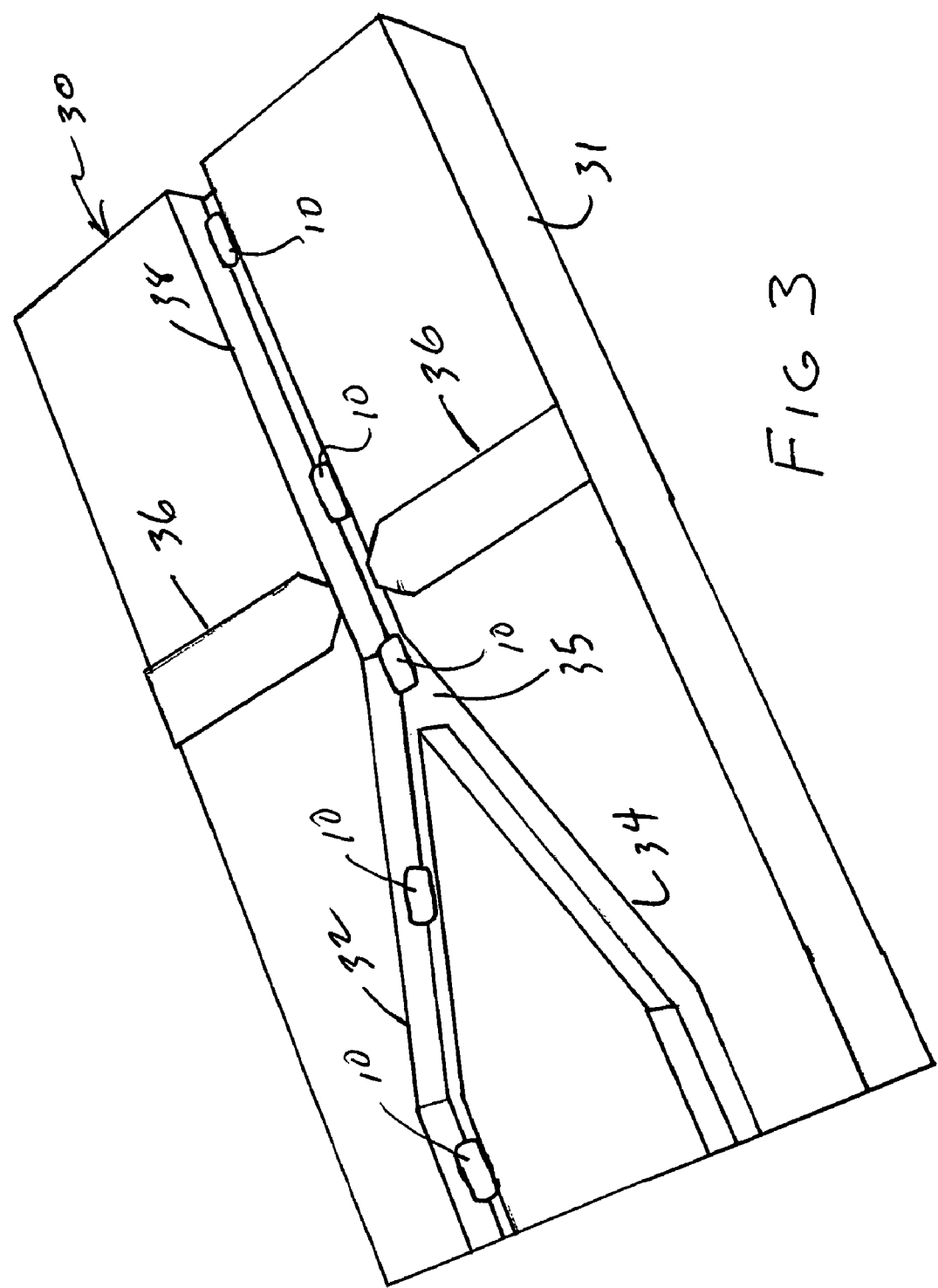

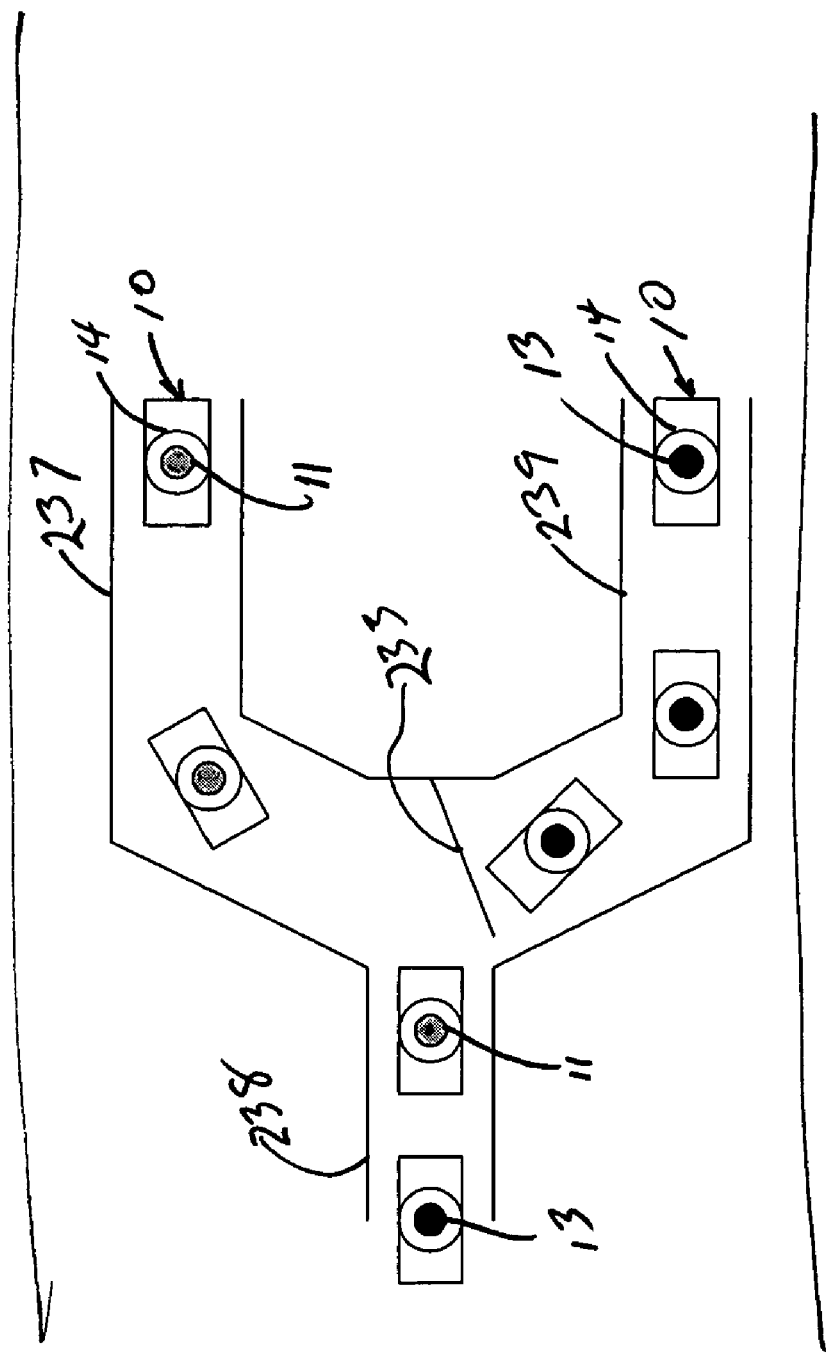

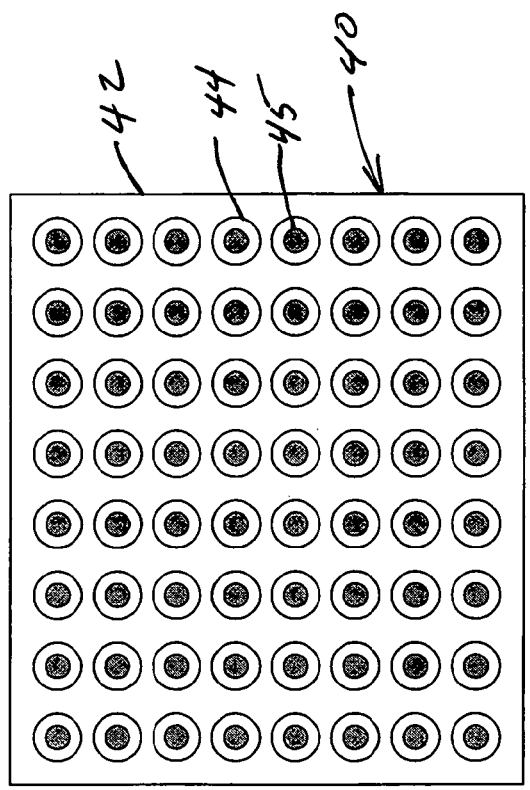
FIG 6A
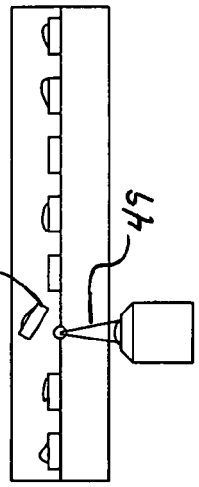
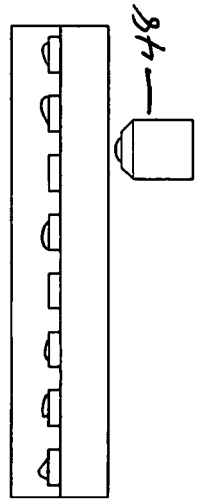
FIG 6B
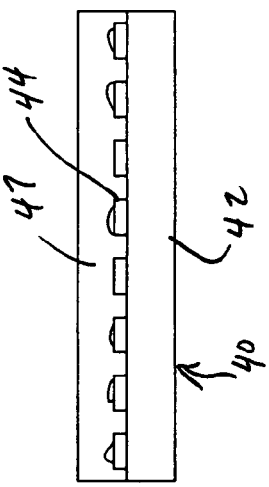

AUTOMATED, PROGRAMMABLE, HIGH THROUGHPUT, MULTIPLEXED ASSAY SYSTEM FOR CELLULAR AND BIOLOGICAL ASSAYS

RELATED APPLICATION

This application claims the benefit of U.S. provisional application Ser. No. 60/564,529 filed Apr. 21, 2004, which application is incorporated herein by reference.

FIELD OF THE INVENTION

The present invention relates to microfabricated devices for single and multiple cell analysis and, more particularly, to devices and methods for performing automated, programmable, high-throughput analysis of adherent cells.

BACKGROUND OF THE INVENTION

Adherent cell assays have typically been performed on slides, in flasks, or in petri dishes. Cells are inspected by microscopy whereby the experimentalist seeks out each cell and images each independently for fluorescence or other indicating measurables of the experiment. Alternatively, the experimentalist may look at the effects of the entire colony of cells as a whole by measuring a global quantity, such as overall fluorescence or absorbance. The methods are not conducive to high throughput analysis, or multiplexed analysis.

Tagged ("bar-coded") microdevices have been developed for the purpose of performing multiplexed assays. Most devices are not suited to carry cells and they do not offer any added functionality other than bar coding. One system currently marketed includes a small metal device that has a bar code pattern etched on it. This enables multiple assays to be performed simultaneously. At the end of the assay, the bar coded "beads" fall to the bottom of the container and they are read by an imaging system. Another system includes beads that can be identified by their adsorption of two dyes in differing ratios, thus enabling bead identification by the use of two photodetectors. This system works in a flow-through manner, but tends not to be able to be used with cells. At least two systems are currently marketed to enhance single cell analysis. One system allows flow-through analysis of single cells by encapsulating the cell in a spherical gel matrix, then flowing the gel balls though the analysis system (e.g., a flow cytometer). Another system provides moderately sized glass plates (0.5 mm×0.35 mm) with color codes on the side to enable cells to plate and be read by imaging. It tends not to be able to be the method used in a flow-through system, nor can the current method of manufacturing enable further miniaturization.

Thus, it is desirable to provide devices and methods that facilitate performing automated, programmable, high-throughput analysis of adherent cells.

SUMMARY

The systems and methods described herein provide for performing high-throughput, programmable, multiplexed assays of biological, chemical or biochemical systems. In one embodiment, a micro-pallet is provided that includes a small flat surface designed for single adherent cells to plate, a cell plating region designed to protect the cells, and shaping designed to enable or improve flow-through operation. The micro-pallets are preferably patterned in such a manner so that they can be readily identified using standard optical equipment.

The micro-pallets are preferably sized to accommodate a single cell and are comparable in size to the cell itself. In this manner, each cell has its own mobile surface. The cell can thus be transported from place to place and be directed into a system similar to a flow cytometer. Furthermore, since the surface itself can be tagged (e.g., a bar code), multiple cells of different origin and history can be placed into the same experiment allowing multiplexed experiments to be performed. The micro-pallet enables adherent cells to be used in flow-through analysis systems such as lab-on-a-chip system.

In another embodiment, the micro-pallets are patterned in an array on a plate.

Other systems, methods, features and advantages of the invention will be or will become apparent to one with skill in the art upon examination of the following figures and description.

BRIEF DESCRIPTION OF THE DRAWINGS

FIG. 1A is a plan view of a micro-pallet of the present invention. The pallet is preferably small enough to carry a single cell.

FIG. 1B is a perspective view of an alternative embodiment of a micro-pallet of the present invention.

FIG. 3 is a perspective view of an electrical poration and loading system that utilizes the micro-pallets shown in FIGS. 1A and 1B.

FIG. 5 is a plan view of flow system having a mechanical means for directing detected cells to different channels.

FIG. 6A is a micro-pallet plate having an array of micro-pallets.

FIG. 6B is a schematic of an imaging system in which the micro-pallet plate is moved through at high speed and a selected plates are released.

DETAILED DESCRIPTION OF THE PREFERRED EMBODIMENT

Figures 2A, 2B:
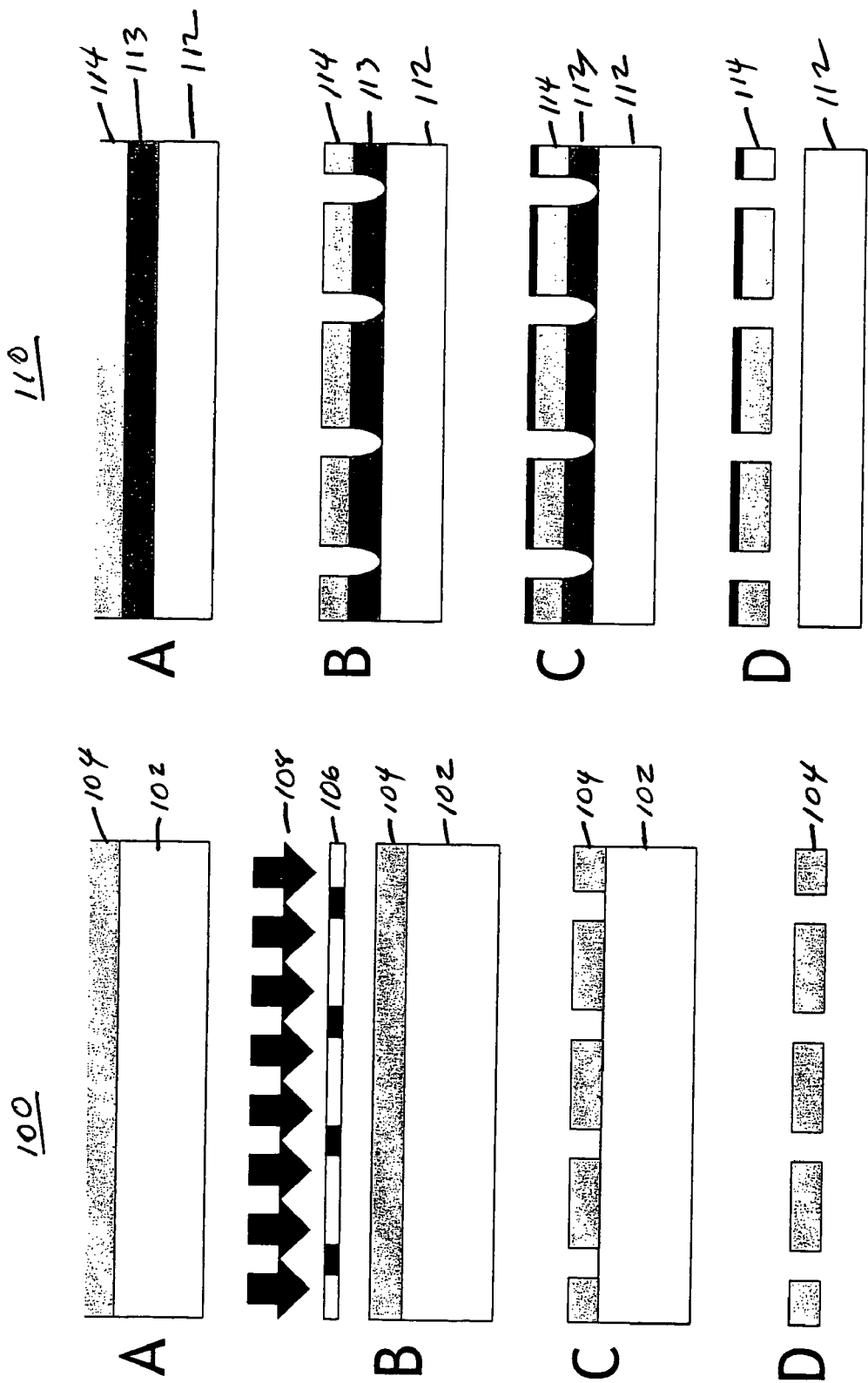
FIGS. 2A and 2B are schematic diagrams of exemplary manufacturing processes for micro micro-pallets shown in FIGS. 1A and 1B.

The systems and methods described herein provide for performing automated, programmable, high-throughput analysis of adherent cells. In a preferred embodiment, microscopic structures such as cell pallets, are manufactured using micromachining techniques. The structures or micro-pallets, which preferably range in size from about ten microns to about one millimeter, and preferably less than five millimeters in any given dimension, are patterned in such a manner so that they can be readily identified using standard optical equipment and designed to carry chemical, biological or living samples through a fluidic system. Preferably, the cell pallets are surface treated to enable adherent cells to plate against them and designed to provide a portable scaffolding for the adherent cells—carrying the cells to different locations through an experimental system such as a flow-through system. For example, the pallets can be run past electrodes for cell wall poration or an optical system designed to detect scattering or fluorescence in a manner similar to a flow cytometer. Typically, flow cytometry cannot be performed on adherent cells because they cannot live in free solution as they require a surface to grow on. The pallets provide the surface to grow on and are constructed to protect the cells from electrical, mechanical and shearing forces and to provide alignment of the pallet in a flow stream, i.e., the pallets can utilize the flow stream to align the cells appropriately.

Additional functions are added by building tagging systems (e.g., bar codes) on the pallets, by adding optical components (e.g., apertures, lenses), or by adding magnetic material to the pallets to allow magnetic sensing or actuation of the pallet. Electrical contacts can be included if desired to facilitate electrical poration of cell walls.

In preferred embodiments, the pallet or micro-pallet is a small, flat piece of material designed to carry molecules, cells, or tissue in a fluid medium. Surface treatments can be provided to affect the adsorption of molecules, cells, or tissue on to the micro-pallet, and produce distinct regions that have biological properties of importance to the cells, such as regions that promote or discourage cell adhesion. The micro-pallet can have markings that vary between opaque and transparent that can encode information about the micro-pallet (e.g., "bar code"). In addition, the micro-pallet can be shaped in a manner that also encodes information about the micro-pallet and/or affect its movement through fluid.

The micro-pallet can be used in a system designed to move the pallet from at least a first location to a second location to (a) perform a step in an assay protocol, or (b) to enhance the ability to detect or image the micro-pallet. External mechanisms, including but not limited to electro-magnetic fields, optical fields, moving surfaces, centrifugal forces, vibration, fluid flow and the like, can be used to move the micro-pallet through the system. The micro-pallet can also be used in a system designed to capture the micro-pallets in fixed locations for the purpose of knowing its location to ease assaying, detection or imaging. The fixed locations can be in array, linear, or any form suitable for the assaying instrument.

Turning in detail to the figures, an embodiment of the micro-pallet is illustrated in FIG. 1A. As depicted, the micro-pallet 10 includes a body 12 preferably formed from metal, glass, polymer or the like with a cell plating region 14 prepared to facilitate cell growth on the micro-pallet 10. The plating region 14 is preferably prepared using a suitable surface coating (e.g., hydrophilic) and can be recessed to protect the cell from harm as the micro-pallet 10 is moved through an experimental system.

Another embodiment of a micro-pallet is illustrated in FIG. 1B. As depicted, the micro-pallet 20 includes a body 22 preferably formed from metal, glass, polymer or the like. A cell plating region 24, prepared using a suitable surface coating (e.g., hydrophilic) to facilitate cell growth, is preferably formed in a recess 28 in the body 22 of the micro-pallet 20. The wall 29 of the recess 28 tends to protect the cell(s) from harm as the micro-pallet 20 is moved through an experimental system.

The shape of the pallet 20 is preferably optimized to enable it to line up in a flow stream. As such, the pallet can be long and thin and can include fins, rudders, or other devices to achieve a desired alignment in a flow stream.

The pallet 20 is preferably made to be opaque, whether through the use of an opaque material or the application of an opaque coating (e.g. thin film of metal). Small openings 26 in the opaque material of the body 22 can be used for identification purposes in the form of a recognizable pattern or, as depicted, a bar code. The bar code 26 can be read by an imaging device or by directing the flow of the pallet 20 past an optical system that can detect the transparent regions of the pallet 20. Alternatively, the pallet 20 can be tagged using conductive patterns, magnetic patterns, or the like.

In addition, the opaque material is preferably patterned to leave a transparent region, which forms an optical aperture, directly below the cell or cell plating region 24 of the body 22. The optical aperture enables imaging of the cell and can reduce optical background.

The pallet 20 can also contain magnetic components to enable electromagnetic sensing and/or actuation of the pallet 20. For example, a pallet 20 containing magnetic components can be moved or directed through a flow system into different channels or reservoirs by application of an external magnetic field.

The micro-pallets 10 and 20 can be manufactured using several methods common to micromachining. In one embodiment, shown in FIG. 2A, the micro-pallets 10 and 20 are manufactured in a process 100 comprising the following steps: (A) a photosensitive polymer 104 is applied to a surface of a substrate 102 formed of glass or the like; (B) the polymer 104 is then photo-patterned 108 through a mask 106 comprising features of interest on the micro-pallets; (C) the polymer 104 is developed, removing unwanted polymer; and (D) the supporting substrate 102 is stripped away leaving freestanding micro-pallets in the polymer material.

In another embodiment, shown in FIG. 2B, the micro-pallets 10 and 20 are manufactured in a process 110 comprising the following step: (A) a structural material 114 is placed over a sacrificial layer of material 113 on a substrate 112 formed of glass or the like; (B) the structural material 114 is etched or cut through to the sacrificial layer 113 using such methods as wet or dry etching, laser ablation, die-stamp cutting, or the like; (C) additional materials (if desired) can be added to the surface of the cut material 114; and (D) the supporting substrate 112 and sacrificial material 113 are stripped away leaving freestanding micro-pallets in the structural material 114.

The small cell pallets 20 and 10 allow adherent cells to be readily stored, transported, and manipulated in a flow-through system. Cells can be visualized one at a time using an imaging system, or they may be detected using optical, electrical, or electromagnetic systems that are configured to detect the cells.

Figure 4:
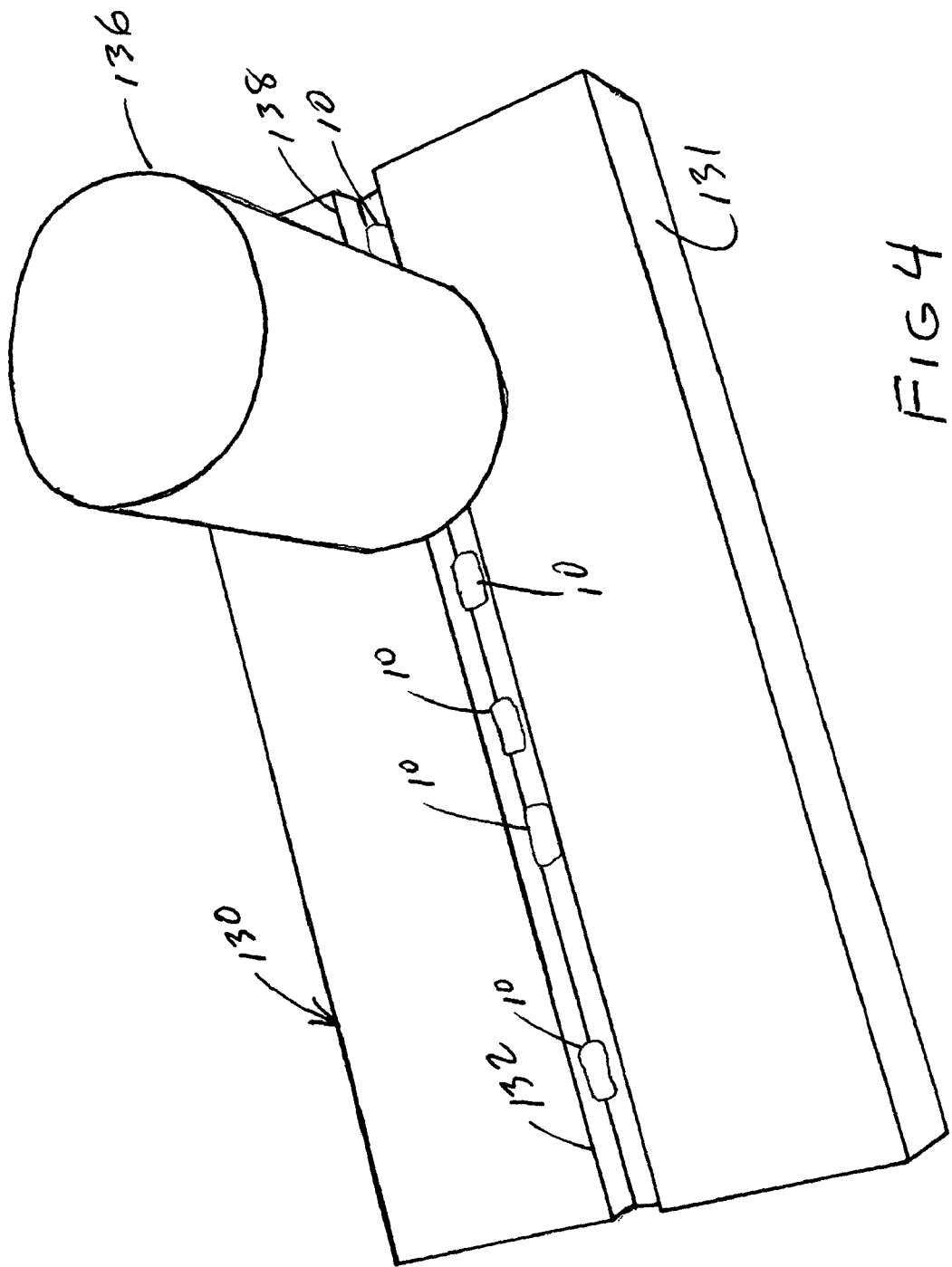
FIG. 4 is a perspective view of an optical readout system for use with the micro-pallets shown in FIGS. 1A and 1B.

Exemplary embodiments of flow-through (lab-on-a-chip) systems that utilize the micro-pallets 20 and 10 are illustrated in FIGS. 3, 4 and 5. Turning to FIG. 3, an electrical poration and cell loading flow through system 30 is illustrated. The system 30, as depicted, is preferably formed in a polymer chip 31 and comprises first and second inlet channels 32 and 34 and an outlet channel 38. A pair of electrodes 36 are positioned along the outlet channel 38 just beyond the junction region 35 of the first and second inlet channels 32 and 34. In this system 30, two or more flow streams flowing through the first and second channels 32 and 34 are brought together at the junction region 35. One of the flow streams flowing through the second channel 34 is preferably a buffer containing a substance intended to be loaded into the cells (e.g., DNA, enzymes, or fluorescent molecules). Another of the flow streams flowing through the first channel 32 contains or transports the micro-pallets 10 and adherent cells plated thereon. The loading reagent comes into close proximity to the micro-pallets 10 as they flow through the channel junction 35. In the embodiment shown, the channels are about 0.5 mm wide and the micro-pallets or carriers 10 are about 0.1 mm wide.

The micro-pallets 10 pass by the two electrodes 36 that carry current (preferably alternating current, to avoid electrolysis). Passing so close to the electrodes 36 tends to ensure that the cells are electrically porated by electrical breakdown of their cell membranes. Following poration, the cells are rapidly loaded with the loading reagent because the loading substance tends to be in very high concentration in regions very close to the porated cells. Serpentine geometries or external magnetic fields can be used to induce mixing and, thus, improve reagent loading.

High speed readout of the cells and pallets may be performed with a suitably designed optical system 130 such as that shown in FIG. 4. In this embodiment, cell pallets 10 are directed into a single file through injection into a laminar flow stream and flow through a channel 132 formed in a polymer chip 131. The injection system (not shown) may include the use of a laminar flow sheath to pinch the cell pallets 10 into alignment. The cell pallets 10 can be aligned through the use of shear forces in a laminar flow stream, or through the use of external magnetic fields (if the cell pallets have magnetic elements). A microscopic imaging system 136 is positioned over the channel 132 adjacent the outlet 138 of the channel 132 to image the cells as they flow past. Imaging preferably occurs by high speed flash and photography, triggered by light scatter from the pallets. Alternatively, imaging can occur by continuous readout of a linear detector array (scanner mode). Other readout systems, including optical systems, electrical systems, and chemical systems can be used.

Other operations, such as directing the micro-pallets 10 into different channels 237 and 239 or reservoir regions, based on preprogramming, or based on detection criteria can be performed, as shown in FIG. 5, to provide automated, programmable sample preparation and cell sorting capabilities. Micro-pallets 10 can be moved using fluid flow, electric fields, magnetic fields or mechanical means. As depicted in FIG. 5, micro-pallets 10 flowing through a channel 238 are directed to different channels. Micro-pallets 10 carrying cells having a first detection criteria 11 are directed to a first channel 237 via mechanical means such as a movable gate 233. Likewise, micro-pallets 10 carrying cells having a second detection criteria 13 are directed to a second channel 239.

Turning to FIGS. 6A and 6B, a micro-machined micro-pallet plate 40 is shown. The pallet plate 40 preferably includes a pre-set array of releasable pallets 44 for cell culturing that are releasably positioned atop of a plate 42 formed of glass or the like. The pallets 44 are treated to promote cell growth at the center 45 of the pallets 44. The pallets 44 are preferably indexed, e.g., bar coded, so that their positions are known in advance of use of the pallet plate 40. Cells are allowed to grow on the pallets 42.

As shown in FIG. 6B, the pallet plate 40, immersed in a buffer solution 47, is moved through an imaging system at a high speed over an imaging device 48. Selected pallets 44A can be released from the surface by a laser pulse 49 and the like.

Figure 7:
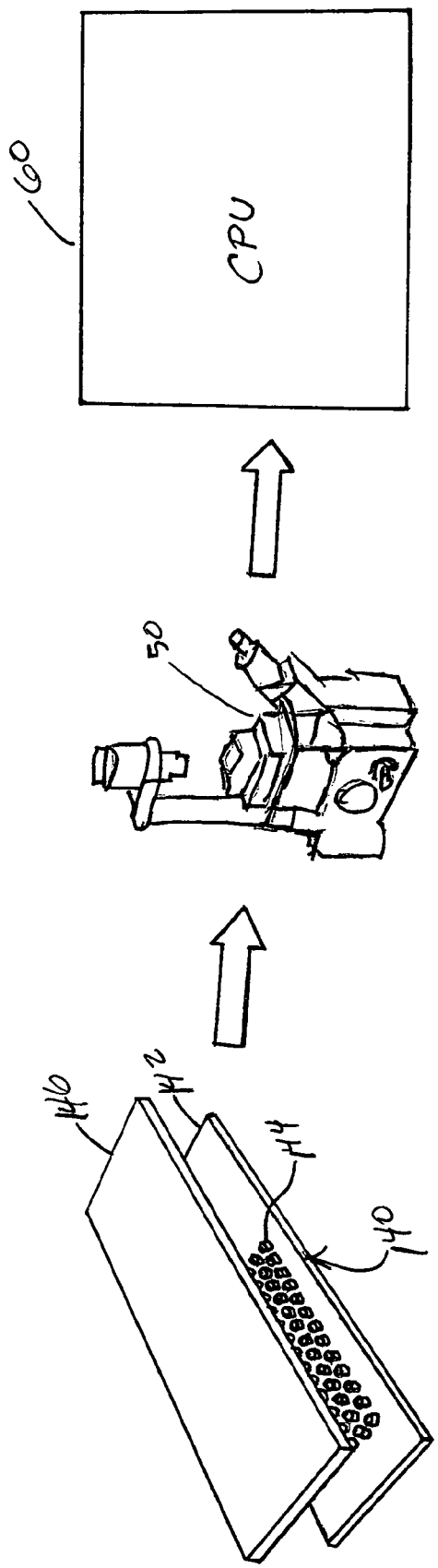
FIG. 7 is a schematic of a high content screening and cell selection system utilizing a micro-pallet cassette comprising an array of micro-pallets.

As shown in FIG. 7, a disposable cassette 140 comprising a substrate or plate 142 formed of glass or the like and a cover 146 can include an array of micro-pallets 144—e.g., providing 500,000 (50×50 microns) pallet sites—positioned on the plate 142. The cassette 140 can be used with a microscope attachment 50 for imaging, fluorescent analysis, sorting, and the like. Analysis software provided on a CPU 60 can be used for high content screening and cell selection. A pallet extractor can be used to extract a selected pallet from the cassette 140.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. In a micro-pallet for an assay flow system having fluid channels wherein the micro-pallet comprising a generally flat shaped body less than 5 mm in any given dimension and adapted to carry biological structures, the improvement being an elongate shaped body with tapered ends and alignment structures extending there from for self alignment in the fluid channels of the flow system to enable identification and analysis as the micro-pallet moves through the fluid channels, and a cell plating region on the body surrounded by a wall positioned along and extending up from the entire periphery of the cell plating region.

2. The micro-pallet in claim 1 wherein the biological structure is a single cell.

3. The micro-pallet in claim 1 wherein the biological structure is tissue.

4. The micro-pallet in claim 1 wherein the body comprises markings that vary between opaque and transparent to encode information about the micro-pallet.

5. The micro-pallet in claim 4 wherein the markings are a bar code.

6. The micro-pallet in claim 1 further comprising information about the micro-pallet encoded in the shape of the body.

7. The micro-pallet in claim 1 further comprising a surface having a surface treatment adapted to affect adsorption of the biological structures.

8. The micro-pallet in claim 1 wherein the shaping of the body is adapted to affect the movement of the body through fluid.

9. The micro-pallet in claim 1 wherein the body includes magnetic components.

10. The micro-pallet in claim 1 wherein the cell plating region is recessed in the body to protect cells plated thereon.

11. A micro-pallet plate comprising
a plate, and
an array of micro-pallets patterned on the plate, each of the micro-pallets having a body with a cell plating region, wherein the body includes alignment structures and is elongate shaped with tapered ends for self alignment into fluid channels of a flow system to enable identification and analysis as the micro-pallets move through the fluid channels, wherein a wall surrounding the cell plating region is positioned along and extends up from the entire periphery of the cell plating region to protect cells plated thereon.

12. The micro-pallet plate in claim 11 wherein the micro-pallet body comprises markings that vary between opaque and transparent to encode unique information about the micro-pallet.

13. The micro-pallet plate in claim 12 wherein the markings are a bar code.

14. The micro-pallet plate in claim 11 wherein the surface of the micro-pallet in the cell plating region having a surface treatment adapted to affect adsorption of cells.

15. The micro-pallet plate in claim 11 wherein the cell plating region is recessed in the micro-pallet to protect cells plated thereon.

16. A flow through experimental system comprising
a chip body,
one or more fluid channels formed in the body, and
one or more micro-pallets located within the one or more fluid channels and moveable between first and second locations within the one or more fluid channels, wherein the one or more micro-pallets having an elongate shaped body with tapered ends and alignment structures extending there from for self alignment into the one or more fluid channels to enable identification and analysis as the micro-pallets move through the fluid channels, wherein the one or more micro-pallets include a cell plating region recessed into the body with the wall of the recess surrounding and extending up from the entire periphery of the cell plating region to protect cells plated thereon.

17. The flow through system of claim 16 further comprising a pair of electrodes.

18. The flow through system of claim 16 further comprising an imaging system.

19. The flow through system of claim 17 further comprising a pallet directing system for directing selected pallets to different locations within the flow through system.

20. The micro-pallet in claim 1 wherein the alignment structures are fin or rudders extending from the body.

21. The micro-pallet plate in claim 11 wherein the alignment structures are fin or rudders extending from the body.

22. The flow through system of claim 16 wherein the alignment structures are fin or rudders extending from the body.

23. The flow through system of claim 16 wherein the pallet directing system includes one or more magnets on the chip body adjacent the one or more channels and one or more magnets in the one or more micro-pallets.

\* \* \* \* \*